United States Patent [19]

Andrade et al.

[11] Patent Number: 4,733,008
[45] Date of Patent: Mar. 22, 1988

[54] PROCESS FOR THE PRODUCTION OF 1,12-DODECANOIC DIACID

[75] Inventors: Juan Andrade, Ridgewood, N.J.; Klaus Koehler, Hainburg; Guenter Prescher, Hanau, both of Fed. Rep. of Germany

[73] Assignee: Degussa Aktiengesellschaft, Frankfurt, Fed. Rep. of Germany

[21] Appl. No.: 77,844

[22] Filed: Jul. 27, 1987

[30] Foreign Application Priority Data

Aug. 23, 1986 [DE] Fed. Rep. of Germany ....... 3628662

[51] Int. Cl.$^4$ .......................................... C07C 51/235
[52] U.S. Cl. .................................... 562/534; 502/152; 502/155; 502/166; 502/213; 502/222; 502/229; 560/190; 562/522; 562/590
[58] Field of Search ............ 562/522, 534, 590; 560/190; 502/152, 155, 166, 213, 222, 229

[56] References Cited

U.S. PATENT DOCUMENTS

| 4,148,822 | 4/1979 | Ogawa et al. | 562/534 |
| 4,404,397 | 9/1983 | Daniel | 562/534 X |
| 4,410,725 | 10/1983 | Decker et al. | 562/534 |
| 4,613,694 | 9/1986 | Rossi et al. | 562/590 |
| 4,634,795 | 1/1987 | Bar-Tana | 562/590 |

Primary Examiner—Werren B. Lone
Assistant Examiner—Vera C. Clarke
Attorney, Agent, or Firm—Beveridge, DeGrandi & Weilacher

[57] ABSTRACT

A process for the production of 1,12-dodecanoic diacid by hydroformylating an olefin in the presence of a rhodium catalyst and oxidation with oxygen of the aldehyde which is thus formed wherein 1,9-decadiene is hydroformylated in the presence of hydridotris-triphenylphosphine-rhodium-carbonyl combined with triphenylphospine and/or triphenylphosphite, and the 1,12-dodecanedialdehyde which was thus formed is oxidized with oxygen in the presence of inorganic or organic Co(II) salts.

12 Claims, No Drawings

PROCESS FOR THE PRODUCTION OF 1,12-DODECANOIC DIACID

The invention relates to a process for the production of 1,12-dodecanoic diacid.

Production of this acid by oxidation and saponification of the methyl-11-aldehyde undecanoate obtained from the hydroformylating of methylundecylenate is known (H. Adkins, G. Krsek, JACS, Vol. 70, January 1948, p. 383-386).

It is also known that hydroformylated products are obtained only on a double bond, if 1,9-decadiene is reacted with carbon monoxide and hydrogen in the presence of a rhodium compound as catalyst.

Undecene aldehydes are obtained in accordance with DE-OS No. 2 724 484 and following oxidation and saponification thereof, the compounds can be used as starting materials according to the Adkins and Krsek process.

It is accordingly an object of the invention to provide a novel process for the production of 1,12-dodecanoic diacid.

It is a feature of the present invention to provide a process for the production of 1,12-dodecanoic diacid by hydroformylation of an olefin in the presence of a rhodium catalyst to produce an aldehyde, followed by oxidation of the aldehyde with oxygen.

It is a further feature of the invention to carry out a hydroformylation of 1,9-decadiene in the presence of a complex that is hydridotris-triphenyl-phosphine-rhodium-carbonyl combined with triphenyl-phosphine and/or with triphenylphosphite to form the 1,12-dodecanediadehyde and then oxidizing the dialdehyde so formed with oxygen in the presence of inorganic or organic Co-(II) salts.

In carrying out the initial steps of the invention, the 1,9-decadiene is selected as the olefin starting material and is then hydroformylated with a gaseous mixture of hydrogen and carbon monoxide in the presence of a catalyst. The reaction generally occurs at temperature of from 70° to 140° C., and preferably at temperatures of from 80° to 120° C. The pressure of the reaction system can be selected from within a wide range, but it is practicable to operate in the pressure range of from 1 to 12 bar. Pressures of from 2 to 8 bar are preferred for purposes of this invention.

It is preferable to use 1.05 to 2.5 times the lowest required stoichiometric quantities of hydrogen and carbon monoxide for the reaction, in which the mole ratio of hydrogen to carbon monoxide can be selected as desired within a wide range, but is preferably between 0.5 to 1.0 to 1.0 to 0.5.

Hydridotris-triphenylphosphine-rhodium-carbonyl complex combined with triphenylphosphine and/or triphenyl-phosphite serves as catalyst during hydroformylating. Such catalysts are described in DE-AS No. 17 93 069 which is incorporated herein by reference. For the execution of the process according to the present invention, it is preferable to use 0.002 to 0.01 parts by weight of the hydridotris-triphenyl-carbonyl and a total of 0.02 to 0.3 parts by weight of the triphenylphosphine and/or triphenylphosphite per part by weight of the 1,9-decadiene. The individual amounts of triphenylphosphine and phosphite when used in combination can vary widely.

The 1,12-dodecane-dialdehyde originating from the hydroformylating reaction is separated from the reaction mixture by distillation in one preferred modification of the process according to the invention and then is oxidized at 10° to 100° C., preferably 40° to 90° C., in the presence of an organic or inorganic Co(II) salt with a gas containing oxygen or else in pure oxygen. It is preferable to use 0.005 to 0.09 parts by weight of the Co(II) salt, especially Co(II) acetate, per part by weight of the 1,12-dodecane-dialdehyde.

In one special embodiment a percarboxylic acid is added to the compound to be oxidized in a quantity of 0.002 to 0.2 parts by weight in relation to the compound. Peracetic and perpropionic acid are preferred for this respect.

The nascent 1,12-dodecanoic diacid crystallizes out of the oxidation mixture following the reaction and after cooling and then is separated by methods known in the art.

In a particular embodiment of the invention, the oxidation reaction is carried out directly in the solution formed during the hydroformylating reaction, and the aforementioned reaction parameters are still retained.

One preferred embodiment in accordance with the present invention is carried out by using an inert organic solvent, preferably an aromatic solvent such as for instance benzene or toluene in the given mixture for hydroformylating of oxidizing.

The present invention will be described in further detail in the following illustrative examples.

EXAMPLE 1

1,9-decadiene (51 g) in 150 ml toluene were placed in an agitated autoclave with 7.9 g triphenylphosphine and 0.48 g hydridotris-triphenyl-phosphine-rhodium-carbonyl complex and then a mixture of equal parts by volume of hydrogen and carbon monoxide were fed into the autoclave reactor under 3 bar pressure. The temperature in the autoclave was held at 80° C.

After 70 minutes no additional gas was absorbed and the feed was terminated. NMR (nuclear magnetic resonance) analysis showed that 98% of the 1,9-decadiene was reacted. The reaction mixture, containing 1,12-dodecane-dialdehyde, was distilled off from the catalyst at a temperature of 125°-130° C. and at a pressure lower than 2 mbar. The yield of 1,12-dodecane-dialdehyde was 57 g (82%).

EXAMPLE 2

The process was carried out as in Example 1, however, after termination of the gas absorption the reaction mixture was converted with 0.87 g of cobalt-(II)-acetate, heated to 60° C., treated with 2 ml 25% perpropionic acid and then was injected with oxygen for about 5 hours. The dodecanoic diacid crystallized out of the reaction mixture upon cooling. The yield was 76% based on the 1,9-decadiene which was used in the reaction.

EXAMPLE 3

5 g of 1,12-dodecane-dialdehyde, as synthesized in Example 1, was dissolved in 50 ml toluene and treated at 60° C. with 30 mg of cobalt-(II)-acetate and 1 ml 25% perpropionic acid and then gaseous oxygen was applied to the mixture for 3 hours. Following draining off of the solvent, 1,12-dodecanoic diacid could be obtained by recrystallization, in a yield of 80% in comparison with the 1,12-dodecane-dialdehyde.

Further variations and modifications of the present invention will be apparent to those skilled in the art from the foregoing and are intended to be encompassed by the claims appended hereto.

The entire disclosure of German priority application No. P36 28 662.1 is relied on and incorporated by reference.

We claim:

1. A process for the production of 1,12-dodecanoic diacid comprising selecting 1,9-decadiene as an olefin and hydroformylating said olefin in the presence of a rhodium complex catalyst to form the corresponding aldehyde in a reaction mixture, said rhodium complex being hydridotris-triphenylphosphine-rhodium-carbonyl combined with triphenylphosphine and/or triphenylphosphite, and thereafter oxidizing the 1,12-dodecane-dialdehyde which is thus formed with oxygen in the presence of an inorganic or organic Co(II) salt.

2. The process as set forth in claim 1, further comprising separating the 1,12-dodecane-dialdehyde from the reaction mixture and then subjecting said dialdehyde to oxidation.

3. The process as set forth in claim 1, wherein the 1,12-dodecane-dialdehyde is oxidized in the reaction mixture.

4. The process as set forth in claim 1, wherein 0.002 to 0.01 parts by weight of hydridotris-triphenyl-phosphine-rhodium-carbonyl and 0.02 to 0.3 parts by weight of triphenylphosphine and/or triphenylphosphite are used for each portion by weight of the 1,9-decadiene.

5. The process as set forth in claim 1, wherein the hydroformylation is carried out at temperatures of from 10° to 100° C. and pressures of from 1 to 12 bar.

6. The process as set forth in claim 1, wherein the oxidation is carried out at a temperature of from 10° to 100° C.

7. The process as set forth in claim 6, wherein the temperature is from 40° to 90° C.

8. The process as set forth in claim 1, wherein from 0.005 to 0.09 parts by weight of the Co(II) salt is used for each part by weight of the 1,12-dodecane dialdehyde.

9. The process as set forth in claim 1, wherein Co(II) acetate is the organic salt.

10. The process as set forth in claim 1, wherein the hydroformylation is conducted with hydrogen and carbon monoxide and hydrogen.

11. The process as set forth in claim 1, further comprising adding a percarboxylic acid to the oxidizing reaction.

12. The process as set forth in claim 11, wherein 0.002 to 0.2 parts by weight of the percarboxylic acid is used for each part by weight of the 1,12-dodecane dialdehyde.

* * * * *